United States Patent [19]

Sasaki et al.

[11] Patent Number: 4,908,311
[45] Date of Patent: Mar. 13, 1990

[54] PROCESS FOR ENZYMATIC PREPARATION OF CELLOOLIGOSACCHARIDES

[75] Inventors: Takashi Sasaki; Hajime Taniguchi; Keiji Kainuma, all of Tsukuba, Japan

[73] Assignee: Director of National Food Research Institute, Ministry of Agriculture, Forestry and Fisheries, Tsukuba, Japan

[21] Appl. No.: 236,555

[22] Filed: Aug. 25, 1988

[30] Foreign Application Priority Data

Apr. 6, 1988 [JP] Japan .................... 63-83139

[51] Int. Cl.$^4$ .................... C12P 19/04; C12P 7/08; C12N 9/42; D21C 1/00
[52] U.S. Cl. .................... 435/101; 435/277; 435/209; 435/252; 435/163
[58] Field of Search .................... 435/101, 99, 277, 209, 435/252, 163, 165, 253

[56] References Cited

PUBLICATIONS

*Chemical Abstracts*, Sasaki et al., Nov. 21, 1983, Vol. 99, No. 21, p. 492, #174207(g).
*Chemical Abstracts*, Mazzaracchio et al., Nov. 21, 1983, vol. 99, No. 21, p. 492, #174210(c).
*Chemical Abstracts*, Breuil et al., Mar. 28, 1977, vol. 86, No. 13, p. 236, #85950(h).
King et al., Disaccharide Preference of an Aerobic ... Received for publication May 5, 1958; pp. 565–570.
Sasaki et al., Bioconversion Cellulose ... Eur J. Appl. Microbiol Biotechnol (1983) 18: 64–66.
Mazzaracchio et al., La Conversione Industriale ... La Chimica El 'Industria V. 65, N.7-8,Lug. AGO 1983, pp. 469–473.
Breuil et al., Cellulase Induction and the Use ... Can. J. Microbiol. vol. 22, 1976 pp. 1776–1781.

*Primary Examiner*—Ronald W. Griffin
*Assistant Examiner*—Pamela S. Webber
*Attorney, Agent, or Firm*—Frishauf, Holtz, Goodman & Woodward

[57] ABSTRACT

A process for enzymatic preparation of cellooligosaccharide from a cellulose-base substance by the action of cellulase produced by an microorganism belonging to the Genus Cellvibrio, wherein an ultrafiltration reactor is used in combination, so that production inhibition can be removed and cellooligosaccharide can be formed and accumulated. The present process permits preparation of cellobiose in high yield and is very advantageous from an industrial standpoint.

7 Claims, 1 Drawing Sheet

PROCESS FOR ENZYMATIC PREPARATION OF CELLOOLIGOSACCHARIDES

BACKGROUND OF THE INVENTION

The present invention relates to a process for enzymatic preparation of cellooligosaccharides.

Cellooligosaccharides are a low molecular weight saccharides comprising glucose molecules linked to one another through a 1,4-β-glucoside bond and constitute the basic structure of cellulose. These cellooligosaccharides are used as a reagent in the study of cellulase. And also, they can be utilized as a food additive, furthermore cellooligosaccharides are expected to find various applications if they are available at low costs.

For chemical preparation of cellooligosaccharides, for example, a method in which purified pulp or cotton is dissolved in a mixed solvent of acetic anhydride and concentrated sulfuric acid to form octaacetate and the octaacetate thus formed is subjected to deacetylation through saponification to obtain the desired cellooligosaccharides, and a chemical method in which cellulose is hydrolyzed with fuming hydrochloric acid/concentrated sulfuric acid and neutralized and, thereafter, fractionated with a carbon celite column to obtain the desired cellooligosaccharides, are known.

These conventional methods, however, cannot be said to be advantageous from an industrial standpoint because the operation of reaction is complicated, or the yield is not sufficiently high.

SUMMARY OF THE INVENTION

As a result of investigations to overcome the above problems of the prior art, it has been found that cellulase produced by microorganisms belonging to the Genus Cellvibrio produces specifically cellobiose from cellulose.

More specifically, it has been found that if cellulase produced by a microorganism belonging to the Genus Cellvibrio is acted on a cellulose-containing substance in an ultrafiltration reactor and a saccharification solution is continuously withdrawn from the reactor, product inhibition can be eliminated and cellooligosaccharides composed mainly of cellobiose can be efficiently formed and accumulated.

The present invention relates to a process for preparing cellooligosaccharides from a cellulose-containing substance in an aqueous medium by the action of cellulase produced by a microorganism belonging to the Genus Cellvibrio, which process is characterized in that a product inhibition is released by using an ultrafiltration reactor in combination, and thus, the formed cellooligosaccharides are effectively accumulated.

BRIEF DESCRIPTION OF THE DRAWING

The Figure shows the results of a paper chromatographic analysis of a composition of an enzymatically decomposed cellulose solution prepared by the process of the present invention. In the Figure, G1 (glucose), G2 (cellobiose), G3 (cellotriose), G4 (cellotetraose) and G5 (cellopentaose) denote standard substances.

DETAILED DESCRIPTION OF THE INVENTION

Figure 1:
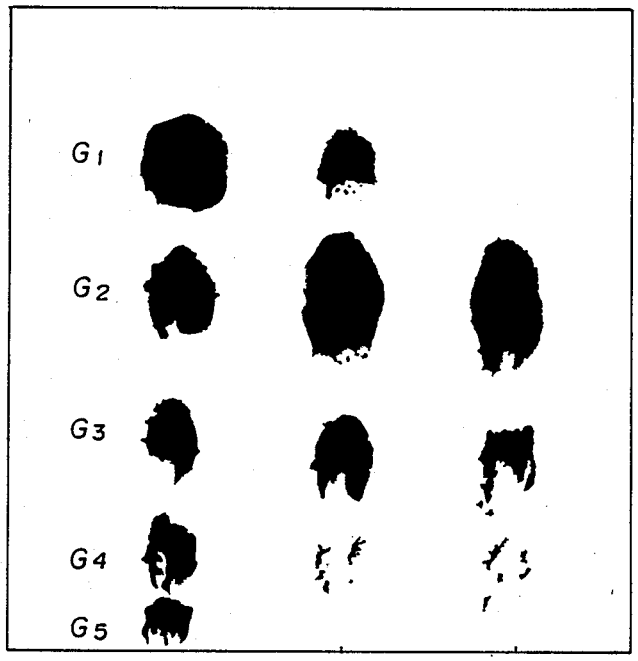

A process for preparation of cellobiose by an enzymatic method with the use of an ultrafiltration reactor in combination has not been known.

An example of an enzyme to be used in the present invention is a cellulase produced by *Cellvibrio gilvus* (ATCC 13127). The cellulase can be accumulated in a culture medium by cultivating the above microorganism with the usual cultivation method. That is, it suffices that the microorganism is cultivated in the usual culture medium containing suitable amounts of a carbon source, a nitrogen source, an inorganic material, amino acid, vitamins and the like under aerobic conditions while controlling the temperature, pH and so on.

The cellulase thus obtained does not always need purification before its use. Usually, cellulase in crude form can be satisfactorily used in the present invention.

Furthermore, the cellulase can be used in an immobilized form or in a free form.

The substrate to be used in the present invention is a cellulose-containing substance and preferably amorphous cellulose. Such amorphous cellulose can be easily obtained, for example, by treating filter paper powder with sulfuric acid for a short period of time. In addition, as the substrate, a biomass resource such as rice straws, rise husks and the like can be used. In this case, it is necessary for the biomass resource to be subjected to de-lignining in advance.

In accordance with the process of the present invention, the aforementioned enzyme and substrate are placed in an ultrafiltration reactor and reacted to obtain the desired cellooligosaccharides.

The substrate is usually suspended in water in such an amount that the concentration of the substrate is about 1 to 10 (w/w%), and the ratio of the substrate to the enzyme (as solids) is about 5:1 to 100:1. Preferably the concentration of the substrate is 3 to 6 (w/w%) and the ratio of the substrate to the enzyme (as solids) is 10:1 to 25:1.

The pH and temperature of the reaction mixture are not critical as long as the enzyme can act on the substrate, thereby producing cellooligosaccharides such as cellobiose and the like. Usually the pH is chosen within the range of 4 to 10 and the temperature, with the range of 30° to 50° C.

The ultrafiltration reactor to be used in the present invention may be of the type that the reactor is combined together with an ultrafiltration membrane, or of the type that the reactor and the membrane are separated from each other.

Any ultrafiltration membrane can be used in the present invention as long as the enzyme does not leak, but an ultrafiltration membrane having a fractional molecular weight of about 1,000 to 20,000 is preferably used.

In the process of the present invention, the saccharification solution resulting from saccharification by the enzymatic reaction is continuously withdrawn from the reactor and, therefore, product inhibition by the formed cellobiose and so on can be removed and the reaction can proceed efficiently (the rate of saccharification is increased by 20 to 30%). In this case, however, it is necessary to maintain the liquid volume at a constant level by supplying a buffer from a reservoir in an amount to compensate for the volume of the liquid withdrawn. In this case, a rate of dilution exerts great influences on the rate of saccharification and is preferably about 0.7 to 1.3.

It is also possible that the reaction is continuously carried out by adding the corresponding amount of the substrate to the saccharified amount.

After the completion of the enzymatic reaction, a saccharification solution composed mainly of cellobiose can be obtained. In some cases, the saccharification solution contains a small amount of glucose. If necessary, therefore, glucose can be completely removed by passing through an immobilized yeast column, for example.

Only cellobiose can be recovered by utilizing a carbon column and so on.

In accordance with the process of the present invention, a large amount of cellobiose can be accumulated, and cellobiose can be obtained in a high yield. Thus the process of the present invention is greatly advantageous from an industrial standpoint.

Cellotriose by-produced in the process of the present invention can be fractionated by the use of a carbon column, for example, if necessary. Thus it is expected to find new applications thereof.

The present invention is described in greater detail with reference to the following example.

EXAMPLE

A mixture of 125 mg of a crude enzyme obtained from a cultivation supernatant of *Celluvibrio gilvus* (ATCC 13127) and 1.25 g of amorphous cellulose was suspended in 25 ml of a 25 mM phosphate buffer (pH 6.5), and the resulting suspension was placed in a 50-milliliter volume ultrafiltration reactor and reacted at 37° C. for 48 hours. An ultrafiltration membrane having a fractional molecular weight of 20,000 was used.

A saccharification solution was continuously withdrawn, and by supplying the buffer from a reservoir in an amount corresponding to that withdrawn, the volume of the liquid was maintained at a constant level. The rate of dilution (D) was 1.0.

The saccharification solution thus obtained was concentrated by the use of an evaporator and freeze dried. A high performance liquid chromatography (HPLC) analysis shown that 0.81 g of cellobiose and 0.21 g of cellotriose were obtained.

A paper chromatographic analysis of the substances confirmed that the Rf values of the substances were in agreement with those of the standard substances as shown in the Figure.

Upon application of $\beta$-glucosidase, both the substances were completely hydrolyzed to glucose, and thus it was confirmed that the substances were cellobiose and cellotriose.

What is claim is:

1. A continuous process for preparing cellooligosaccharide from a cellulose-containing substance in an aqueous medium comprising the steps of, in a reaction vessel, reacting the cellulose in the aqueous medium with cellulase produced by a microorganism designated cellvibrio gilvus, to produce a saccharification solution including the cellooligosaccharide and the reaction products;

continuously separating the saccharification solution from the cellulose to obtain the cellooligosaccharide; and continuously adding aqueous medium to the reaction vessel to replace separated saccharification solution, and wherein the reaction vessel is an ultrafiltration reactor and the continuous separation step comprises ultrafiltering the saccharification solution using a membrane having a fractional molecular weight of 1,000 to 20,000 and removing the filtered saccharification solution from the reactor.

2. The process of claim 1 wherein the cellulose is from rice straw or rich husks, further comprising delignining the rice straw or husks and thereafter mixing a delignined product with water in such an amount that the concentration of the product is about 1 to 10 percent by weight.

3. The process of claim 2 wherein the ratio of substrate to enzyme in the reactor is 10:1 to 25:1.

4. The process of claim 3 wherein the pH of the aqueous medium is 4 to 10 and the reaction is run at a temperature of 30° C. to 50° C.

5. The process of claim 3 wherein the ratio of substrate to enzyme in the reactor is 10:1 to 25:1.

6. The process of claim 1 wherein the pH of the aqueous medium is 4 to 10 and the reaction is run at temperature of 30° C. to 50° C.

7. The process of claim 1 wherein the cellulose containing substance is amorphous cellulose.

* * * * *